US007867552B2

(12) United States Patent
Serban et al.

(10) Patent No.: US 7,867,552 B2
(45) Date of Patent: Jan. 11, 2011

(54) METHODS FOR USE OF A SENSITIVE LAYER FOR HYDROGEN SULPHIDE DETECTION WITH SAW/BAW DEVICES

(75) Inventors: Bogdan-Catalin Serban, Bucharest (RO); Viorel-Georgel Dumitru, Ploiesti (RO); Cornel P. Cobianu, Bucharest (RO); Stefan-Dan Costea, Bucharest (RO); Nicolae Varachiu, Bucharest (RO); Stefan I. Voicu, Bucharest (RO)

(73) Assignee: Honeywell International Inc., Morristown, NJ (US)

( * ) Notice: Subject to any disclaimer, the term of this patent is extended or adjusted under 35 U.S.C. 154(b) by 360 days.

(21) Appl. No.: 12/116,778

(22) Filed: May 7, 2008

(65) Prior Publication Data

US 2009/0280031 A1 Nov. 12, 2009

(51) Int. Cl.
*G01N 27/416* (2006.01)
*B05D 5/12* (2006.01)

(52) U.S. Cl. .................................. 427/100; 422/83
(58) Field of Classification Search ................ 427/100; 422/83
See application file for complete search history.

(56) References Cited

U.S. PATENT DOCUMENTS

| | | | |
|---|---|---|---|
| 6,951,690 B2 | 10/2005 | Katz et al. | 428/447 |
| 2008/0229831 A1 * | 9/2008 | Serban et al. | 73/589 |

OTHER PUBLICATIONS

Sensing CO2 in a Chemically Modified Porous Silicon Film; M. Rocchia, E. Garrone, F. Geobaldo, L. Boarino, M.J. Sailor; Phys. Stat. Sol. (2) 197, No. 2, 365-369 (2003)/DOI 10, 1002/pssa. 200306526.

Covalently Anchored Supramolecular Monolayers on Quartz Surfaces for Use in SAW Sensors; P. A. Lieberzeit, W. Greibl, H. Stathopulos, F.L. Dickert, G. Fisherauer, W. Bulst; Elsevier Science, Sensors and Actuators B 113 (2006) 677-683.

The First Single-Step Immobilization of a Calix-[4]-arene onto the Surface of Silica; A. Katz, P. D. Costa, A.C.P. Lam, J. M. Notestein; American Chemical Society, Chem. Mater. 2002, 14, 3364-3368.

Surface Acoustic Wave Microsensors Based on Cyclodextrin Coatings; D. Li, M. Ma; Elsevier Science, Sensors and Actuators B 69 (2000) 75-84.

(Continued)

*Primary Examiner*—Michael Barr
*Assistant Examiner*—Ryan Schiro
(74) *Attorney, Agent, or Firm*—Kermit D. Lopez; Luis M. Ortiz; Kris T. Fredrick

(57) ABSTRACT

Methods can be adapted for design of a sensitive monolayer for detection of hydrogen sulphide at room temperature with SAW/BAW devices. The sensitive monolayer can be synthesized based on chemical compounds, which belongs to a class of thiacalix[n]arenas, mercapto halides, mercapto alcohols and chloromethylated thiacalix[n]arenas. The sensitive monolayer can be directly immobilized or anchored at the surface of a piezoelectric quartz substrate in a covalently bonded manner by means of direct printing process. The piezoelectric quartz substrate can be activated in basic medium or in acid medium before the immobilization of the sensitive monolayer in order to increase the population of OH groups. Thus, the synthesized sensitive monolayer exhibits a high site density, fast response and long-term stability for $H_2S$ sensing.

8 Claims, 7 Drawing Sheets

OTHER PUBLICATIONS

Recent Advances in the Functionalizations of The Upper Rims of Thiacalix[4]Arenes. A Review.; S. Parola, C. Desroches; Collect. Czech. Chem. Commun. (vol. 69 (2004).

Upper Rim Substituted Thiacalix[4]Arenes; O. Kasyan, D. Swierczynski, A. Drapailo, K. Suwinska, J. Lipkowski, V. Kalchenko; Science Direct, Tetrahedron Letters 44 (2003) 7167-7170.

* cited by examiner

METHODS FOR USE OF A SENSITIVE LAYER FOR HYDROGEN SULPHIDE DETECTION WITH SAW/BAW DEVICES

TECHNICAL FIELD

Embodiments are generally related to solid-state sensors for hydrogen sulphide detection. Embodiments are particularly related to methods for design of a sensitive layer for hydrogen sulphide detection with SAW/BAW devices. Embodiments are additionally related to a SAW/BAW based hydrogen sulphide sensor with the sensitive layer.

BACKGROUND OF THE INVENTION

Hydrogen sulphide ($H_2S$) is a flammable, irritating, corrosive, bad-smelling gas with very high toxicity. Toxicity of the hydrogen sulphide is comparable with hydrogen cyanide, which is considered as a broad-spectrum poison. Hydrogen sulphide can affect different parts and systems such as skin, eyes and throat in the human body, depress the nervous system and eventually cause death. Hydrogen sulphide occurs naturally in the environment, but ultra low levels can be tolerated because the human body can possess a number of enzymes that are able to perform the conversion through oxidation of hydrogen sulphide to sulphate. Thus, the detection of $H_2S$ is a major challenge for air quality monitoring.

It is important to continually sense the hydrogen sulphide to provide safeguards for employees who work in areas like petrochemical and fuel refinery industry where exhibits $H_2S$ is exhibited. The detection of hydrogen sulphide is also very beneficial for the biomedical field, especially for determination of $H_2S$ content in mouth air and for diagnosis in dentistry. Semiconductor oxides play a significant role for $H_2S$ sensing. Tin dioxide-based materials such as pure $SnO_2$, $CuO$—$SnO_2$ and $SnO_2$—$Ag_2O$ can easily sense $H_2S$ in air. Copper oxide can be a best promoter for the $SnO_2$-based hydrogen sulphide sensors; however, such sensors exhibit maximum sensitivity at elevated temperatures, (i.e. around 150° C.). At this elevated temperature, irreversible reactions can take place between the gas and the sensing layer, which affects the long-term stability of the sensor.

The majority of prior art gas sensors utilize a thin solid film on a SAW/BAW device to overcome the aforementioned drawbacks. In such gas sensors, gas molecules are absorbed onto the surface of solid film due to interactions such as hydrogen bond, electrostatic, pi-pi stacking, Van Der Waals interactions and host-guest relationship. Therefore, the propagation velocity of the SAW/BAW acoustic waves can be alerted as a function of the gas and eventually a shift in the phase or resonance frequency of SAW/BAW devices induced. Sputtered inorganic film based on activated tungsten trioxide materials, (e.g. pure tungsten trioxide, doped tungsten trioxide with iridium, gold and palladium), can be developed to form a sensitive film for hydrogen sulphide detection. Such thin films exhibit a good sensitivity toward hydrogen sulphide, but unfortunately the temperature still remains too high, (i.e. around 130° C.).

Recently, calixarenes have been used to achieve organic compounds with versatile applications such as gas sensors, solar cells, batteries, antistatic coatings, electro-luminescent devices, electrodes, nonlinear optical devices, transistors, etc. Therefore, sensitive layers can be made using calixarenes and related compounds for $H_2S$ detection. But, the immobilization of calixarenes and related compounds at the surface of a piezoelectric substrate can require laborious synthesis of calixarene derivatives, which contain reactive functional groups for polymerization to the surface of the piezoelectric substrate. Such functional groups are typically linked to the lower rim of the calixarene or other related compounds via flexible tethers.

A need therefore exists for an improved method for design of a sensitive layer with high sensitivity, which enables hydrogen sulphide detection at room temperature with SAW/BAW devices. Such an improved method is described in greater detail herein.

BRIEF SUMMARY

The following summary is provided to facilitate an understanding of some of the innovative features unique to the embodiments disclosed and is not intended to be a full description. A full appreciation of the various aspects of the embodiments can be gained by taking the entire specification, claims, drawings, and abstract as a whole.

It is, therefore, one aspect of the present invention to provide an improved method for the design of a sensitive monolayer for detection of hydrogen sulphide at room temperature.

It is another aspect of the present invention to provide for a SAW/BAW based hydrogen sulphide sensor with the sensitive monolayer.

The aforementioned aspects and other objectives and advantages can now be achieved as described herein. An improved method for design of a sensitive monolayer for detection of hydrogen sulphide at room temperature with SAW/BAW devices. The sensitive monolayer can be synthesized based on chemical compounds, which belongs to a class of thiacalix[n]arenas, mercapto halides, mercapto alcohols and chloromethylated thiacalix[n]arenas. The sensitive monolayer can be directly immobilized or anchored at the surface of a piezoelectric quartz substrate in a covalently bonded manner by means of direct printing process. The piezoelectric quartz substrate can be activated in basic medium or in acid medium before the immobilization of the sensitive monolayer in order to increase the population of OH groups. Thus, the synthesized sensitive monolayer exhibits a high site density, fast response and long-term stability for $H_2S$ sensing.

Furthermore, the sensitive monolayer of chemical compounds can interact with $H_2S$ by dipole-dipole forces in accordance with features of the present invention. The sensitivity of the sensitive monolayer is improved due to the presence of mercapto groups in mercapto alcohols and mercapto halides, and/or due to the presence of sulphur atoms in thiacalixarenes and chloromethylated thiacalixarenes. The immobilization of the sensitive monolayer can be performed in a nitrogen atmosphere in order to avoid oxidation of phenolic groups.

In addition, the sensitive monolayers can be placed on surface acoustic wave (SAW)/bulk acoustic wave (BAW) devices, as described in paragraph 10. The sensitive monolayers can additionally be consolidated by thermal annealing or laser annealing under ambient conditions in order to obtain the stable sensing monolayer. The sensitive monolayer made up of such chemical compounds with mercapto groups or derivatives of thiacalixarenas can achieve effective detection of hydrogen sulphide at room temperature. Such sensitive monolayers are widely utilized in different areas such as high temperature gas sensors like $H_2S$ sensor, gas turbines, automotive applications, etc.

BRIEF DESCRIPTION OF THE DRAWINGS

The accompanying figures, in which like reference numerals refer to identical or functionally-similar elements throughout the separate views and which are incorporated in and form a part of the specification, further illustrate the embodiments and, together with the detailed description, serve to explain the embodiments disclosed herein.

DETAILED DESCRIPTION

The particular values and configurations discussed in these non-limiting examples can be varied and are cited merely to illustrate at least one embodiment and are not intended to limit the scope thereof.

Figure 4:
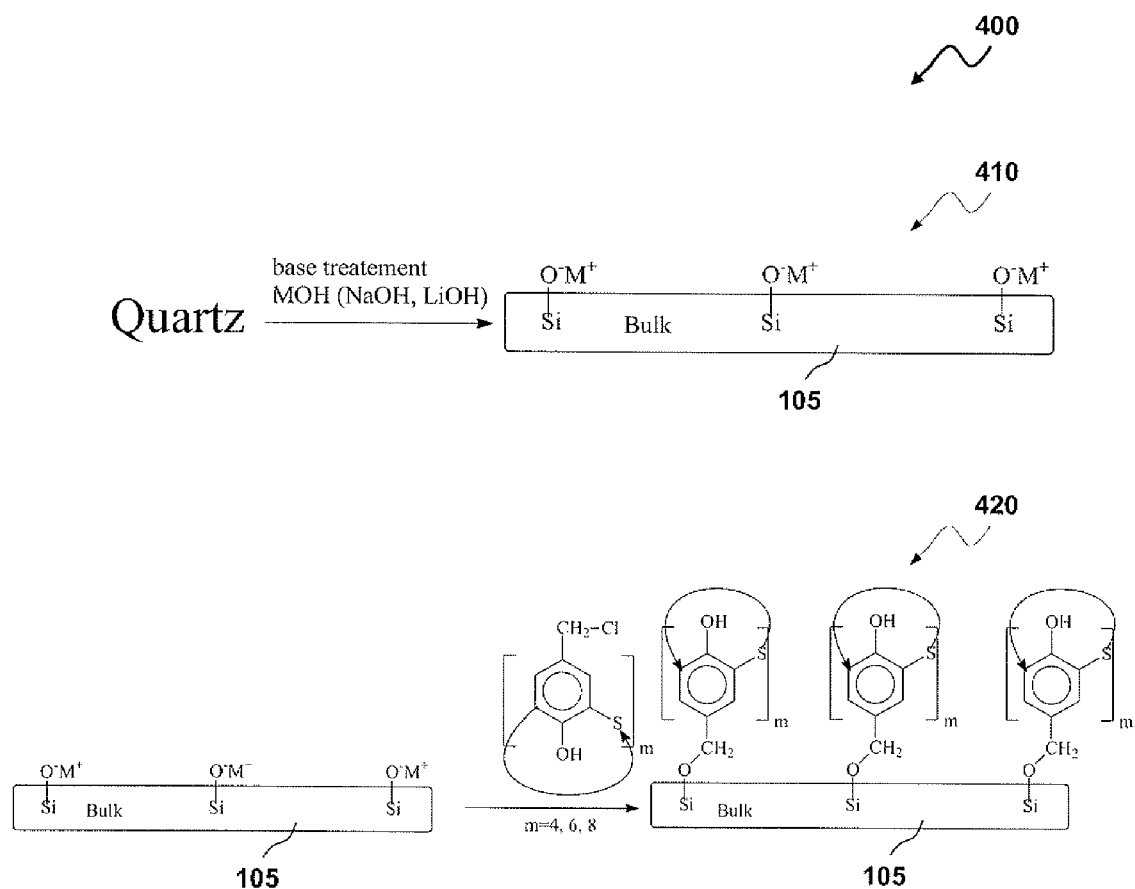
FIG. 4 illustrates a schematic diagram of a process for on-chip immobilization of chloromethylated thiacalix[n]arenes at the surface of the piezoelectric quartz substrate, which can be implemented in accordance with an alternative embodiment.
Figure 5:
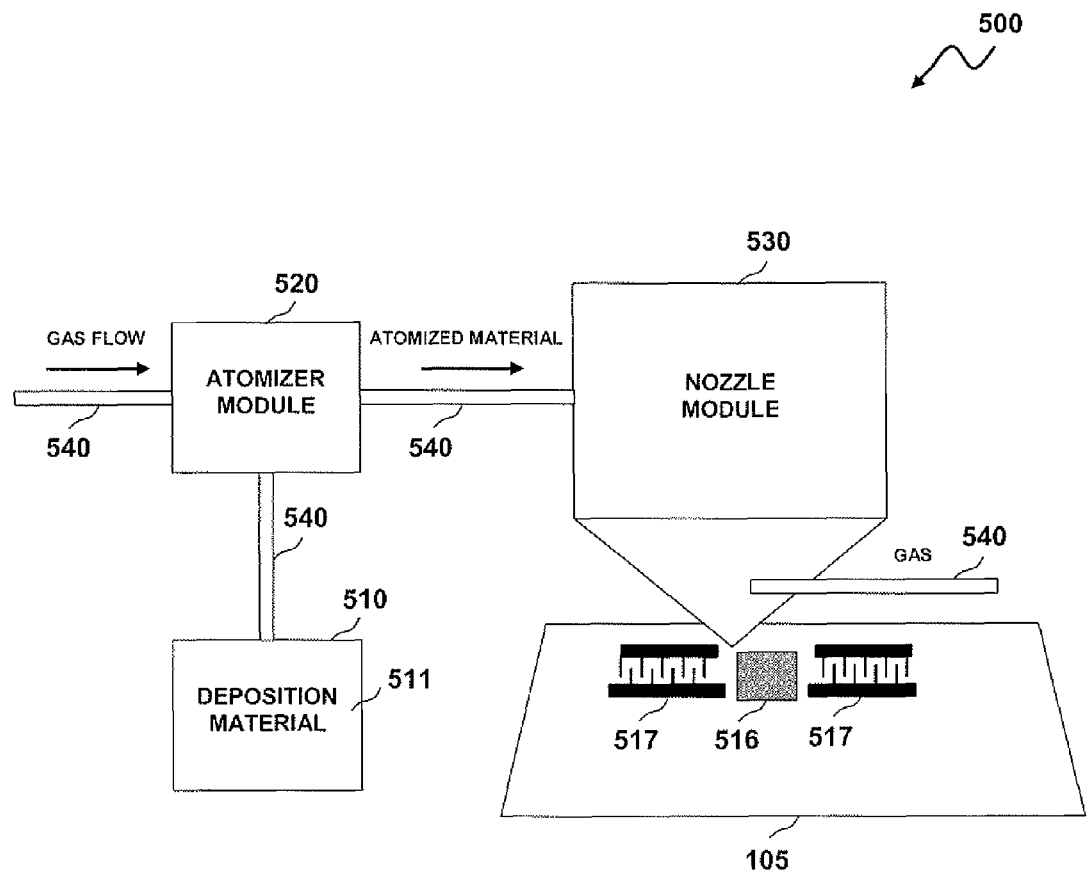
FIG. 5 illustrates a general schematic diagram of a system for direct printing of a sensing monolayer on a SAW device, which can be implemented in accordance with a preferred embodiment.

The present embodiment utilizes four approaches to perform immobilization of sensing monolayers 516 onto the surface of a piezoelectric quartz substrate 105, as shown in FIG. 5, to provide a sensor adapted for hydrogen sulphide SAW/BAW detection. The approaches can be based on immobilization of thiacalix[n]arenes through the intermediate of a spacer in the piezoelectric quartz substrate 105, immobilization of mercapto halides, immobilization of mercapto alcohols, and immobilization of chloromethylated thiacaliz[n]arenes. FIGS. 1-4 can respectively describe each immobilization approach in greater detail.

Figure 1:
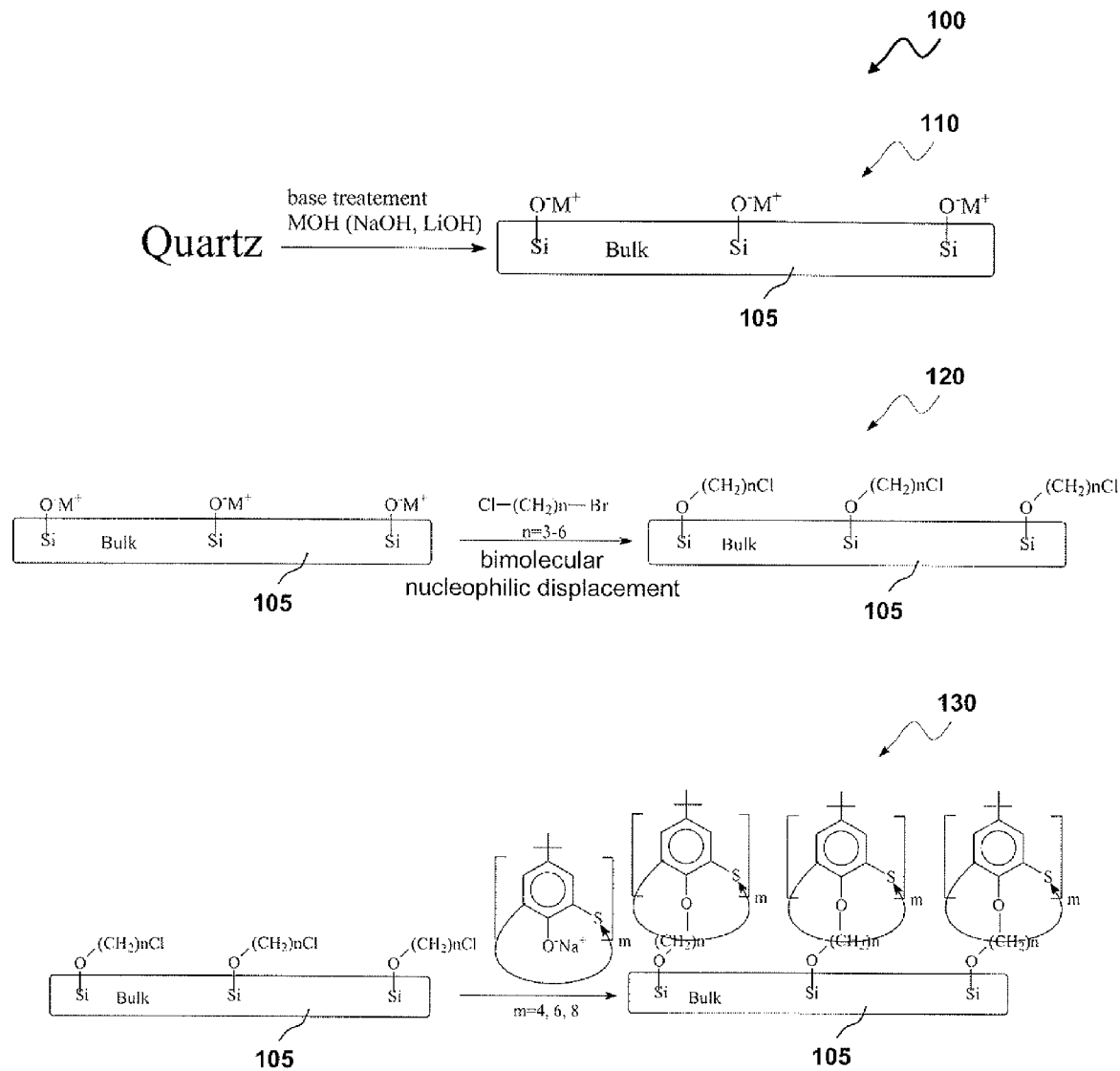
FIG. 1 illustrates a schematic diagram of a process for on-chip immobilization of p-tert-butylthiacalix[n]arenes at the surface of a piezoelectric quartz substrate, which can be adapted for use in implementing a preferred embodiment.

Referring to FIG. 1, a schematic diagram of a process 100 for on-chip immobilization of p-tert-butylthiacalix[n]arenes at the surface of a piezoelectric quartz substrate 105 is illustrated, which can be adapted for use in implementing a preferred embodiment. In the step 110, as depicted in FIG. 1, the surface of the quartz plate 105 can be chemically modified with 0.25 M solution of natrium hydroxide for 10 minutes in order to increase the population of anions O—. Thus, the anions are available for bimolecular displacements in a Williamson-type synthesis. The modified quartz plate 105 containing O—Na+ ionic sites at the top can be reacted with $\alpha,\omega$ dihaloalkanes with two different halogen atoms to exhibit different reactivities in bimolecular displacements, as shown in step 120. The $\alpha,\omega$ dihaloalkanes are selected from 1-bromo-3-chloropropane, 1-bromo-4-chlorobuthane, 1-bromo-5-chloropentane and 1-bromo-6-chlorohexane. The bromo atoms can be reacted initially, since the bromo atoms are more reactive than chloro atoms. In the step 130, the p-tert-butylthiacalix[n]arene is immobilized at the surface of the quartz plate 105, after the quartz plate 105 is reacted with $\alpha,\omega$ dihaloalkanes. The sensitivity of a resulting sensitive monolayer film can be ensured by the presence of the sulphur atoms that are incorporated in the structure of macrocyclic ligand. Dipole-dipole forces can exist between the polar molecules of hydrogen sulphide and the sulphur atoms of supramolecular compound.

For example, the piezoelectric quartz substrate 105 can be subjected to pre-treatment and activated with the solution of natrium hydroxide for 10 minutes. The activated quartz substrate 105 can be placed in a 0.5 M solution of 1-bromo-5-chloropentane in toluene for 1 hour under argon atmosphere at elevated temperature (100° C.). Thus, a functionalized quartz substrate 105 with pre-linkers with terminal chloro atoms can be synthesized. Simultaneously, a suspension of 0.3 mmol thiacalix[4]arene in a mixture of toluene (50 ml) and dimethyl formamide (50 ml) can be prepared. Then 0.3 mmol of NaOH (aqueous solution) is added in order to convert the hydroxyl groups in O— anions. The final mixture can be sonicated in an ultrasonical bath for 4 hours. These preparations can be performed in a nitrogen atmosphere in order to avoid the oxidation of phenolic groups. After that, a solution of deprotonated thiacalixarene can be directly deposited on the surface of the functionalized quartz substrate 105 by means of direct printing method. Finally, the quartz substrate 105 can be washed with absolute chloroform, washed with DI water, and dried in nitrogen atmosphere for 1 hour.

The synthesis of sensing monolayer film can be based on thiacalix[n]arenes, where n=4, 6, 8. The thiacalix[n]arenes is covalently bonded at the surface of the piezoelectric quartz substrate 105. The synthesis of sensitive monolayer film can include pre-treatment of the quartz substrate 105 with the mixture of trichloroethylene and ethanol at 1:1 ratio for 20 minutes. Then the quartz substrate 105 is rinsed with acetone and finally with isopropylic alcohol in order to remove the organic contaminants, which exist at the surface of the quartz substrate 105. Thereafter, the quartz substrate 105 can be washed with deionized (DI) water in two steps in order to completely remove the remaining organic solvents at the top of the quartz plate 105. Finally, the quartz plate 105 is dried in a hot air stream.

Figure 2:
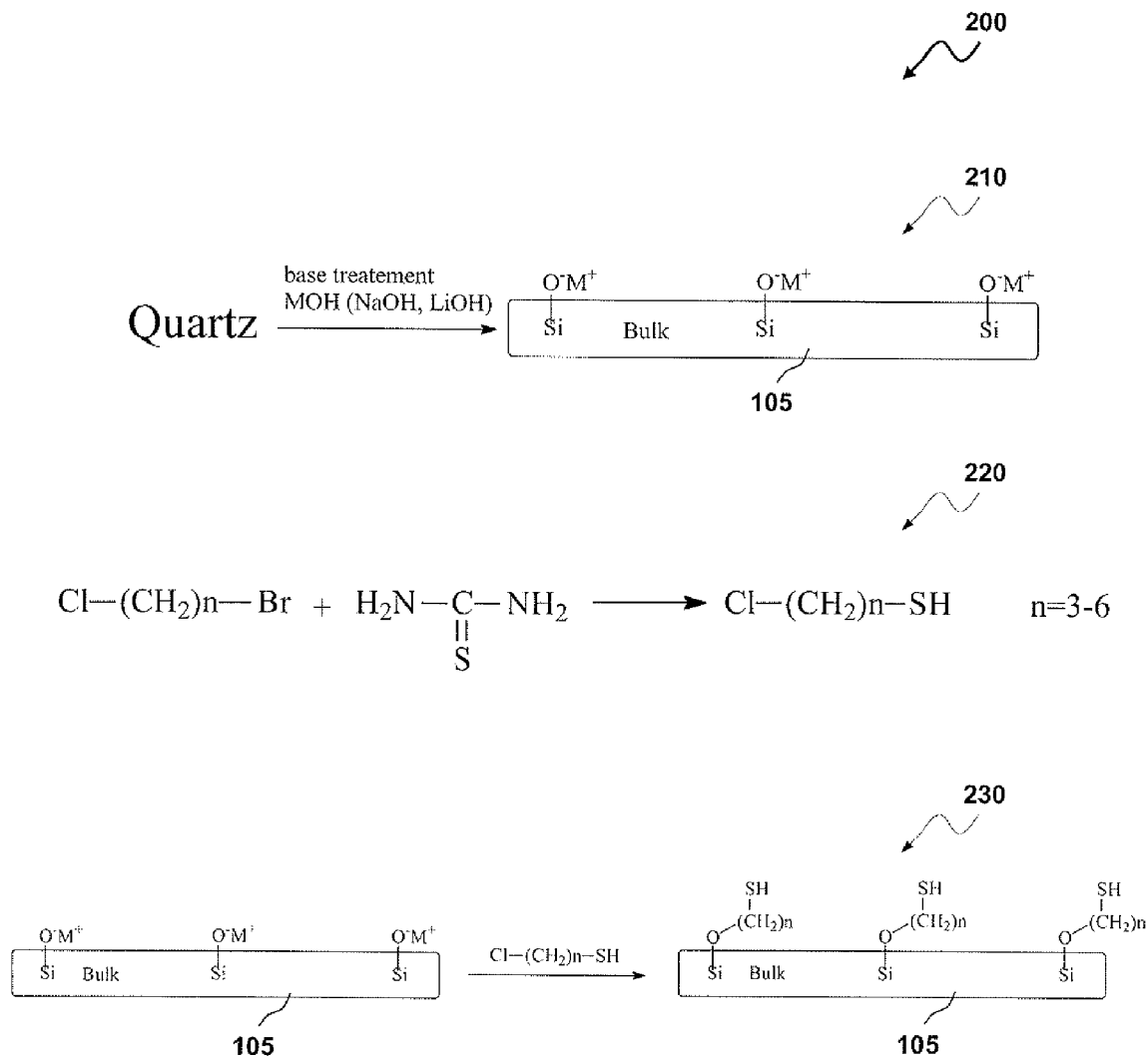
FIG. 2 illustrates a schematic diagram of a process for on-chip immobilization of mercapto halides at the surface of the piezoelectric quartz substrate, which can be implemented in accordance with an alternative embodiment.

Referring to FIG. 2, a schematic diagram of a process 200 for on-chip immobilization of mercapto halides at the surface of the piezoelectric quartz substrate 105 is illustrated, which can be implemented in accordance with an alternative embodiment. In FIG. 2, the synthesis of a sensing monolayer film can be based on mercapto halides, which is covalently bonded at the surface of the piezoelectric quartz plate 105. The quartz plate 105 can be pretreated similarly as described in FIG. 1. In the step 210, as depicted in FIG. 2, the surface of the quartz plate 105 is chemically modified with 0.25 M solution of natrium hydroxide for 10 minutes in order to increase the population of anions O— for bimolecular displacements in a Williamson-type synthesis.

Simultaneously, a mercapto halide can be prepared from $\alpha,\omega$ dihaloalkanes with two different halogen atoms and thiourea, as shown in step 220. The $\alpha,\omega$ dihaloalkanes are selected from 1-bromo-3-chloropropane, 1-bromo-4-chlorobuthane, 1-bromo-5-chloropentane and 1-bromo-6-chlorohexane. After that, a solution of mercapto halide in toluene can be directly deposited or immobilized on the surface of the functionalized quartz plate 105 by means of direct printing method, as depicted in step 230. Finally, the quartz plate 105 is washed with absolute chloroform and dried at 100° C. under vacuum to remove the solvent. The sensitivity of a resulting sensing monolayer film is ensured by the presence of the mercapto groups that are located at the end of the alkylic chain. Dipole-dipole forces can exist between the polar molecules of hydrogen sulphide and sulphur atoms of terminal mercapto groups.

Figure 3:
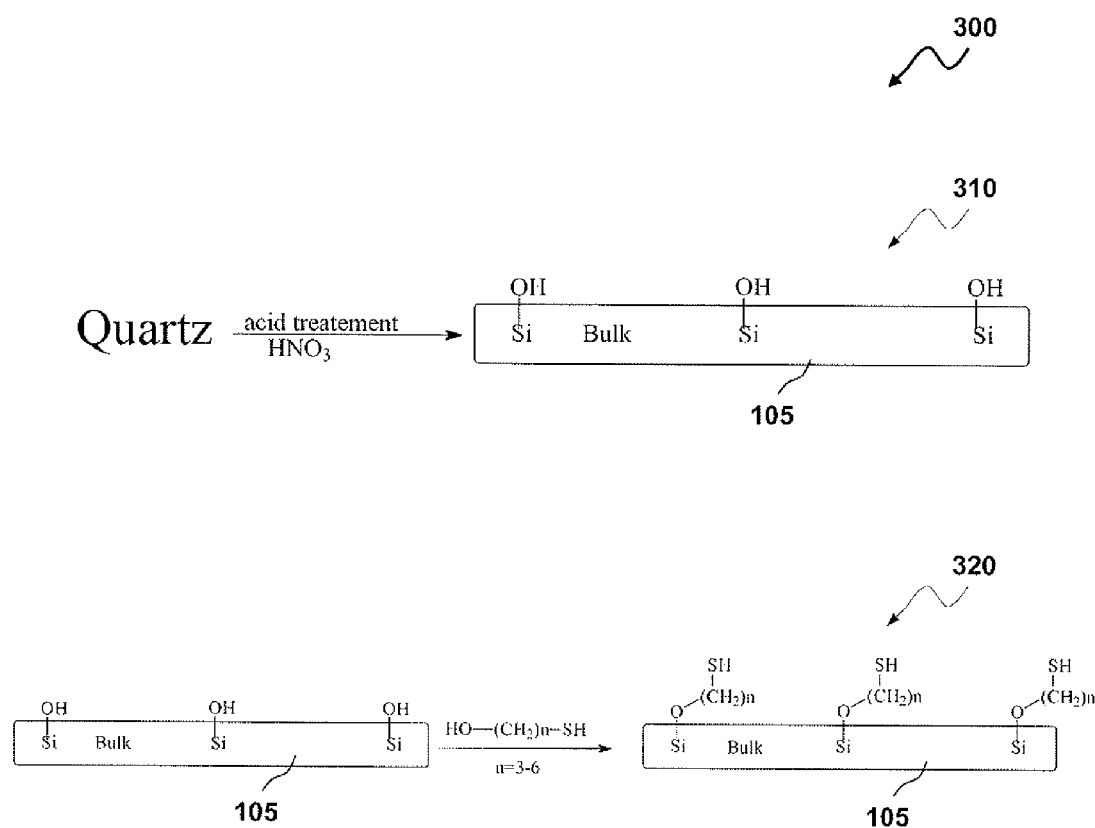
FIG. 3 illustrates a schematic diagram of a process for on-chip immobilization of mercapto alcohols at the surface of the piezoelectric quartz substrate, which can be implemented in accordance with an alternative embodiment.

Referring to FIG. 3, a schematic diagram of a process 300 for on-chip immobilization of mercapto alcohols at the surface of the piezoelectric quartz substrate 105 is illustrated, which can be implemented in accordance with an alternative embodiment. In FIG. 3, the synthesis of sensing monolayer film can be based on mercapto alcohols, which is covalently bonded at the surface of the piezoelectric quartz substrate 105. Initially, the quartz plate 105 can be pretreated with the mixture of trichloroethylene and ethanol at 1:1 ratio for 20 minutes. Then the quartz plate 105 is rinsed with acetone and finally with isopropylic alcohol such that the organic contaminants at the surface of the quartz plate 105 can be removed. After that, the quartz plate 105 is washed with deionized (DI) water in two steps in order to dispose of the remaining organic solvents at the top of the quartz plate. Finally, the quartz plate 105 can be dried in a hot air stream. In the step 310, the cleaned quartz plate 105 is subjected to treatment with concentrated nitric acid to increase the number of hydroxilic groups for the further polycondensation.

In the step 320, as described in FIG. 3, the modified surface of the quartz plate 105 can react with mercapto alcohols at elevated temperature by means of polycondensation in order to perform anchoring at the surface of the quartz plate 105 through the intermediate of covalent bond. The mercapto alcohols are selected from a group consisting of 1-mercapto-2-propanol, 3-mercapto-1-propanol, 4-mercapto-1-buthanol, 3-mercapto-2-buthanol, 5-mercapto-1-penthanol, and 6-mercapto-1-hexanol. Thereafter, the quartz plate 105 with the sensing monolayer can be washed with absolute chloroform and dried at 100° C. under vacuum to remove the solvent. Such sensing monolayer is attached through the strong covalent bond at the surface of the quartz plate 105, which yields a compact and robust design for SAW-BAW sensors. The mercapto groups in the molecular structure of mercapto alcohols are the responsible atoms or groups of atom for $H_2S$ sensing. The SAW device is loaded and a shift in propagation velocity of surface acoustic wave is recorded as a phase shift in SAW delay line due to the dipole-dipole forces between hydrogen sulphide molecules and SH moieties.

For example, the quartz plate 105 is initially subjected to the pre-treatment and activated with 25 ml concentrated nitric acid and DI water. The activated piezoelectric substrate 105 can be placed in a 100 ml flask and added with 10 ml of 4-mercapto-1-buthanol. Then the flask can be heated in an oven at 150° C. for 4 hours in argon atmosphere. Finally, the functionalized quartz plate 105 is rinsed with isopropilic alcohols and dried under nitrogen at 100° C.

Referring to FIG. 4, a schematic diagram of a process 400 for on-chip immobilization of chloromethylated thiacalix[n]arenes at the surface of the piezoelectric quartz substrate 105 is illustrated, which can be implemented in accordance with an alternative embodiment. In FIG. 4, the synthesis of sensing monolayer film can be based on chloromethylated thiacalix[n]arenes (where n=4, 6, 8), which is covalently bonded at the surface of the piezoelectric quartz substrate 105. The quartz plate 105 can be pretreated similarly as described in FIG. 1.

In the step 410, as depicted in FIG. 4, the surface of the quartz plate 105 is chemically activated with 0.25 M solution of natrium hydroxide for 10 minutes to increase the population of anions O— for bimolecular displacements in a Will-iamson-type synthesis. In the step 420, the modified quartz 105 with O—Na+ ionic sites at the top can be reacted with chloromethylated thiacalix[n]arenas via bimolecular nucleophilic displacement. The sensitivity of the sensing monolayer film can be enhanced due to the presence of the sulphur atoms that are incorporated in the structure of macrocyclic ligand. Dipole-dipole forces can exist between the polar molecules of hydrogen sulphide and the sulphur atoms of supramolecular compound.

For example, the piezoelectric quartz substrate 105 is subjected to pre-treatment and activated with 0.3 M solution of natrium hydroxide for 20 minutes. The activated quartz substrate 105 can be placed in a 0.5 M solution of chloromethylated thiacalix[n]arenes in toluene for 1 hour under argon atmosphere at elevated temperature, (i.e. 100° C.). Then a phase transfer catalyst, in particular 0.005 mmol solution of cetyl trimethyl ammonium bromide, can be added to the quartz substrate 515. Finally, the quartz substrate 105 is washed with absolute chloroform, washed with DI water, and dried in nitrogen atmosphere for 1 hour.

Referring to FIG. 5, a general schematic diagram of a system 500 for direct printing of a sensing monolayer 516 on a piezoelectric quartz substrate 105 for a SAW chemical sensing device is illustrated, which can be implemented in accordance with a preferred embodiment. The system 500 can include a module 510 containing a deposition material 511 in liquid phase, an atomizer module 520 and a nozzle module 530. The deposition material 511 is a solution selected from a group of thiacalix[n]arenes, mercapto halides, mercapto alcohols and/or chloromethylated thiacalix[n]arenes. The module 510 can supply the deposition material 511 to the atomizer module 520 via a supply tube 540 after synthesizing one of the solutions of thiacalix[n]arenes, mercapto halides, mercapto alcohols and/or chloromethylated thiacalix[n]arenes.

The atomizer module 520 can transform the liquid phase of the desired deposition material 511 into colloidal suspensions, (i.e. into the atomized state). Then the colloidal suspensions are transported to a nozzle module 530 with the help of carrier gas flow applied on the supply tube 540. The nozzle module 530 can directly anchor or immobilize the well-controlled droplets of the deposition material 511 onto a piezoelectric quartz substrate 105. Then the piezoelectric quartz substrate 105 with the deposition material can be washed with absolute chloroform and dried either in nitrogen atmosphere for 1 hour or at 100° C. under vacuum in order to obtain a stable sensing monolayer 516 on the quartz substrate 105.

Figure 6:
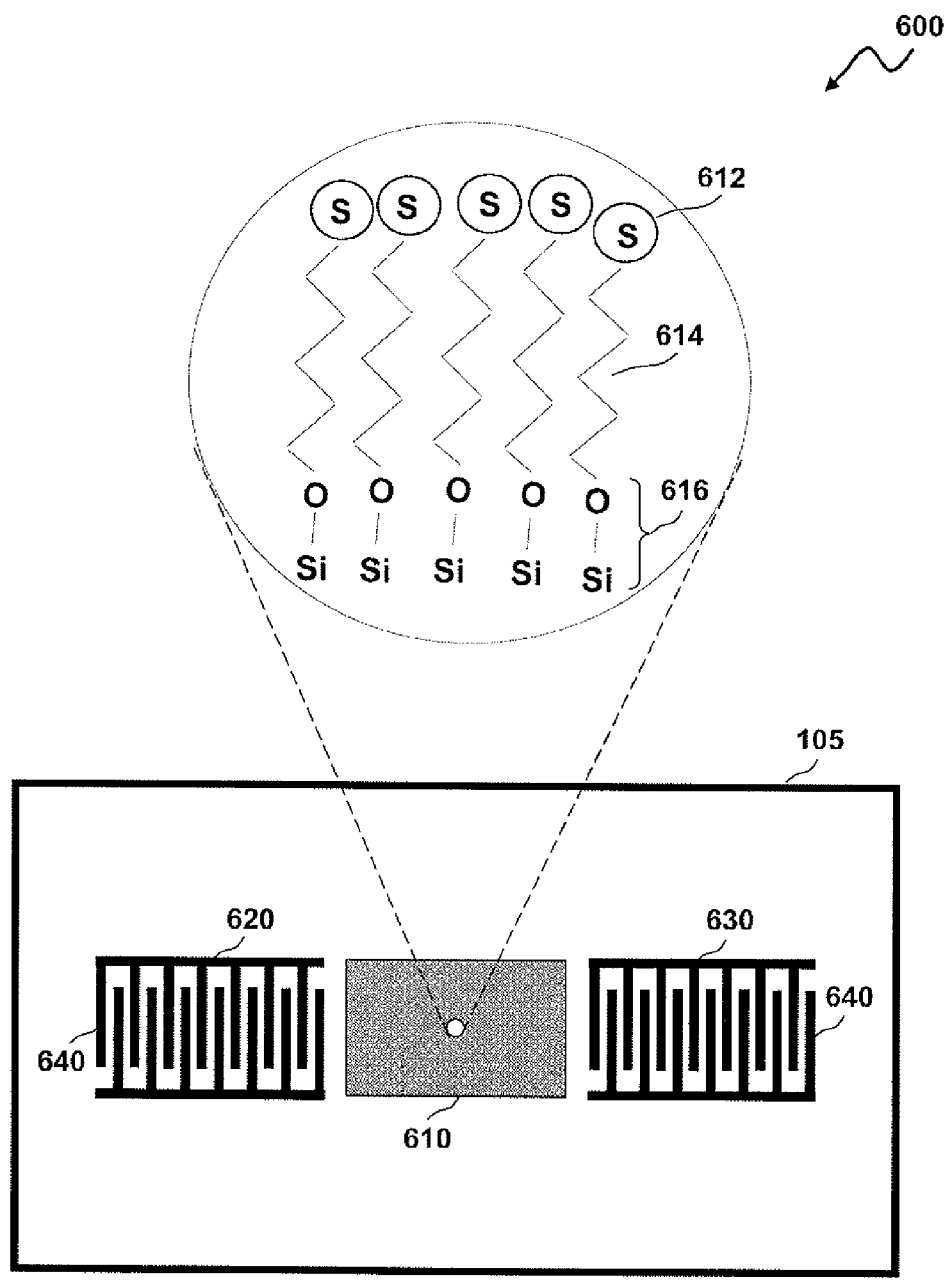
FIG. 6 illustrates a general schematic diagram of a delay line SAW chemical sensor with covalently bonded sensing monolayer deposited between two interdigital transducers (IDT), which can be implemented in accordance with a preferred embodiment.

In addition, the sensing monolayer 516 can be placed in between interdigital transducers 517, which acts as a SAW device, in particular SAW chemical sensor 600, as shown in FIG. 6. The selective application of the sensing monolayer 516 in the specific regions of the solid state quartz substrate 105 can be done by means of direct printing method. The direct printing being an additive maskless deposition method does not imply etching away the deposited material, so there is no concern about selectivity between organic material and photoresist masking layer during etching, as in the case of spin coating/spray coating methods. Thus, the direct printing method saves the amount of liquid material utilized for obtaining the sensing monolayer 516.

Referring to FIG. 6, a general schematic diagram of a delay line SAW chemical sensor 600 with covalently bonded sensing monolayer 610 deposited between two interdigital transducers (IDT) 620 and 630 is illustrated, which can be implemented in accordance with a preferred embodiment. The SAW chemical sensor 600 is configured in a delay line configuration for $H_2S$ sensing, (i.e. the output signal of the SAW sensor 600 is delayed relative to the input signal). The SAW chemical sensor 600 can include a sensing monolayer 610 and two interdigital transducers 620 and 630. The interdigital transducers are made of noble metal, like gold, provided with an adhesion layer, like Ti, to assure that metallization survives the chemical attack during quartz surface functionalization. In the delay line SAW sensor 600, the delay time is partially related to the amount of chemical sensed by the sensing monolayer 610. The delay time is also related to the spacing between the interdigital transducers 620 and 630. The sensing monolayer 610 can be designed based on thiacalix[n]arenas, mercapto halides, mercapto alcohols and chloromethylated thiacalix[n]arenes. The sensing monolayer 610 can be covalently bonded with the piezoelectric quartz substrate 105 in a space between the input interdigital transducer 620 and the output interdigital transducer 630 with the help of direct printing method.

The interdigital transducers 620 and 630 are adapted to produce a different acoustic wavelength, which can be determined by a line width and spacing of interdigital electrode fingers 640 of each interdigital transducer 620 and 630. The interdigital electrode fingers 640 of each interdigital transducer 620 and 630 are electrically coupled via capacitive coupling. The interdigital transducers 620 and 630 are electrically bonded to the piezoelectric quartz substrate 105. When an AC signal is applied to the interdigital transducers 620 and 630, an electric field is produced between the individual electrode fingers 640. Thus, the quartz substrate 105 exhibits the piezoelectric effect to cause a mechanical displacement such that the input interdigital transducers 620 can generate a surface acoustic wave in the piezoelectric quartz substrate 105.

Thereafter, the surface acoustic wave can pass the sensing monolayer 610, which includes mercapto groups or thiacalix-arenes 612, spacers with 1 to 6 carbon atoms 614 and activated quartz groups 616. The sensing monolayer 610 can interact with the hydrogen sulphide at room temperature by dipole-dipole forces. The shift in phase or frequency of the surface acoustic wave in the presence of the $H_2S$ gas takes place due to the changes in the mercapto groups or thiacalix-arenes 612 after exposure at the hydrogen sulphide. The output interdigital transducer 630 can receive the surface acoustic wave after passing the sensing monolayer 610. Then the output interdigital transducer 630 produces an output signal related to the amount of hydrogen sulphide sensed by the sensing monolayer 610 and in response to the received surface acoustic wave. Such sensing monolayer 610 can also be immobilized on the piezoelectric quartz substrate 105 of a BAW (bulk acoustic wave) device (not shown).

Figure 7:
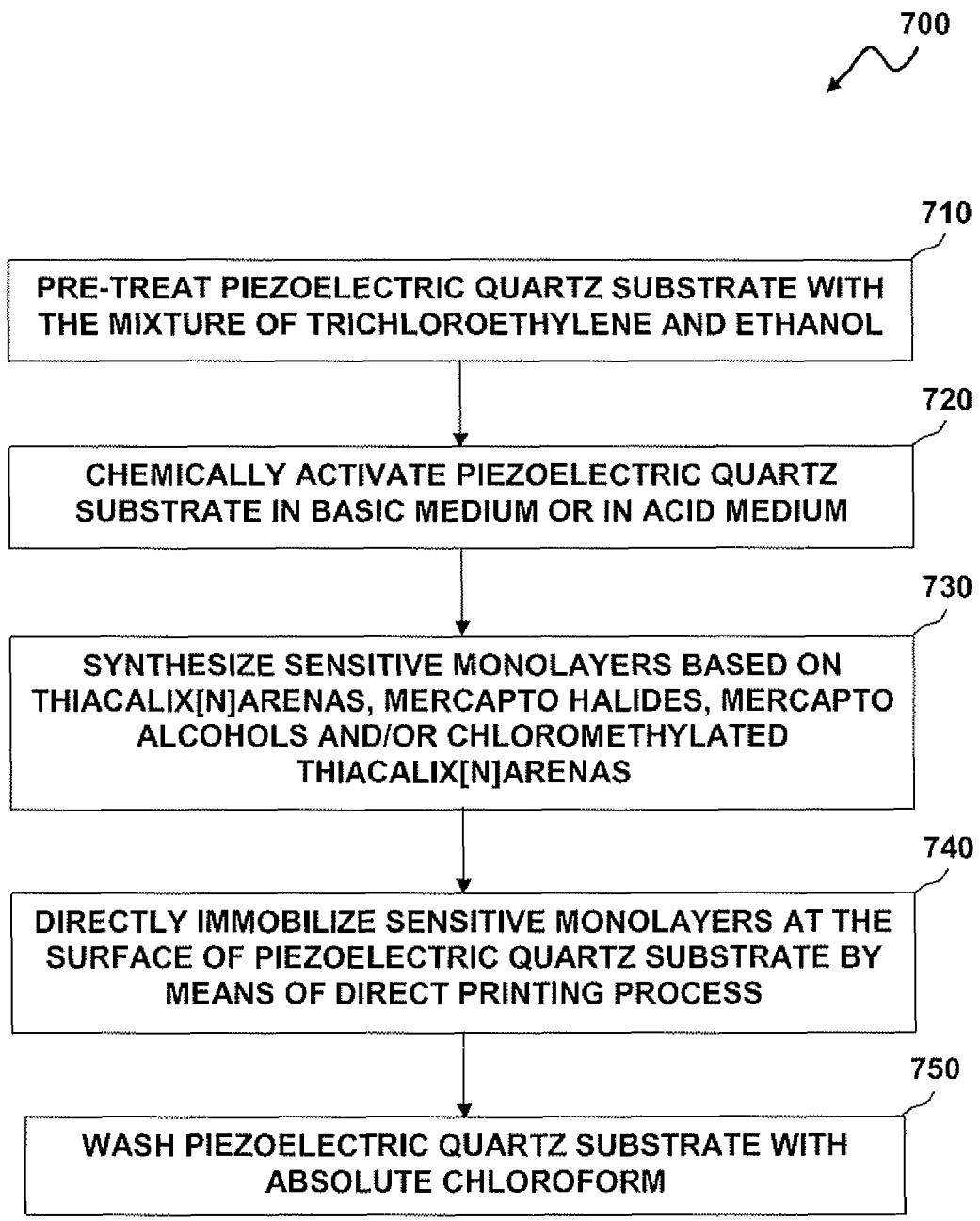
FIG. 7 illustrates a flowchart of a method for design of a sensing monolayer for detection of hydrogen sulphide at room temperature, which can be implemented in accordance with a preferred embodiment.

Referring to FIG. 7, a flowchart of a method 700 for design of a sensing monolayer 516 and 610 for detection of hydrogen sulphide at room temperature is illustrated, which can be implemented in accordance with a preferred embodiment. As illustrated at block 710, a piezoelectric quartz substrate 105 can be pre-treated with the mixture of trichloroethylene and ethanol and also rinsed with acetone and isopropylic alcohol in order to remove the organic contaminants at the surface of the quartz substrate 105. As depicted at block 720, the quartz substrate 105 can be chemically activated in basic medium or in acid medium in order to increase the population of OH groups.

Thereafter, as mentioned at block 730, the sensitive monolayers 516 and 610 are synthesized based on chemical compounds, which belongs to a class of thiacalix[n]arenas, mercapto halides, mercapto alcohols and chloromethylated thiacalix[n]arenas. As depicted at block 740, the sensitive monolayers 516 and 610 can be directly immobilized or anchored at the surface of the functionalized quartz substrate 105 in a covalently bonded manner by means of direct printing process. As illustrated at block 750, the quartz substrate 105 can be washed with absolute chloroform in order to obtain the stable sensing monolayers 516 and 610 on the quartz substrate 105. The stable sensitive monolayers 516 and 610 can exhibit a high site density, fast response and long-term stability for $H_2S$ sensing.

It will be appreciated that variations of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. A method providing sensing monolayers for hydrogen sulphide detection, said method comprising:
   synthesizing a sensing monolayer based on at least one chemical compound, wherein said at least one chemical compound comprises thiacalix[n]arenas, mercapto halides, mercapto alcohols and chloromethylated thiacalix[n]arenas;
   directly depositing said sensing monolayer at the surface of a piezoelectric quartz substrate in a covalent bonded manner by means of direct printing process; and
   chemically activating said piezoelectric quartz substrate in a basic medium and/or in an acid medium before the immobilization of said sensing monolayer in order to increase the population of OH groups, wherein said sensing monolayer and said piezoelectric quartz substrate are associated with at least one SAW/BAW device.

2. The method of claim 1 wherein said sensing monolayer interacts with the hydrogen sulphide at room temperature by means of dipole-dipole forces.

3. The method of claim 1 wherein said mercapto halides are prepared from α,ω dihaloalkanes selected from a group comprising: 1-bromo-3-chloropropane, 1-bromo-4-chlorobutane, 1-bromo-5-chloropentane and 1-bromo-6-chlorohexane.

4. The method of claim 1 wherein said mercapto alcohols comprises 1-mercapto-2-propanol, 3-mercapto-1-propanol, 4-mercapto-1-buthanol, 3-mercapto-2-buthanol, 5-mercapto-1-penthanol and 6-mercapto-1-hexanol.

5. The method of claim 1 wherein said piezoelectric quartz substrate is pre-treated with a mixture of trichloroethylene and ethanol and is rinsed with acetone and isopropylic alcohol.

6. The method of claim 1 wherein said piezoelectric quartz substrate is washed with absolute chloroform and dried in a hot air stream.

7. The method of claim 1 wherein said basic medium comprises alkaline hydroxide and said acid medium comprises concentrated nitric acid.

8. The method of claim 1 wherein said sensing monolayer is utilized in a SAW/BAW based hydrogen sulphide sensor.

* * * * *